United States Patent
Cutting

(10) Patent No.: US 10,031,033 B2
(45) Date of Patent: Jul. 24, 2018

(54) MONITORING OF THE FREEZING STATE OF A BIOPHARMACEUTICAL FLUID FOUND IN A CONTAINER

(71) Applicant: SARTORIUS STEDIM NORTH AMERICA INC., Bohemia, NY (US)

(72) Inventor: Jonathan Cutting, Hannover (DE)

(73) Assignee: SARTORIUS STEDIM NORTH AMERICA INC., Bohemia, NY (US)

( * ) Notice: Subject to any disclaimer, the term of this patent is extended or adjusted under 35 U.S.C. 154(b) by 317 days.

(21) Appl. No.: 14/779,193

(22) PCT Filed: Mar. 20, 2014

(86) PCT No.: PCT/EP2014/055563
§ 371 (c)(1),
(2) Date: Sep. 22, 2015

(87) PCT Pub. No.: WO2014/147158
PCT Pub. Date: Sep. 25, 2014

(65) Prior Publication Data
US 2016/0047764 A1    Feb. 18, 2016

(30) Foreign Application Priority Data

Mar. 22, 2013 (FR) ...................... 13 52589

(51) Int. Cl.
*G01K 11/28* (2006.01)
*A01N 1/02* (2006.01)
(Continued)

(52) U.S. Cl.
CPC ............ *G01K 11/28* (2013.01); *A01N 1/0252* (2013.01); *A01N 1/0263* (2013.01); *G01K 11/06* (2013.01); *F25D 19/00* (2013.01)

(58) Field of Classification Search
CPC ........ G01K 11/28; G01N 2009/026–2009/028
(Continued)

(56) References Cited

U.S. PATENT DOCUMENTS 2,634,605 A * 4/1953 Shea ...................... G01N 7/00
374/55
3,730,500 A    5/1973 Richards
(Continued)

FOREIGN PATENT DOCUMENTS

CH        648412 A5 *    3/1985 ......... G05D 23/1923
DE    102011003441 A1 *  8/2012 ........... F28D 20/021
(Continued)

OTHER PUBLICATIONS

French Preliminary Search Report, dated Oct. 23, 2013, from corresponding French Application.
(Continued)

*Primary Examiner* — Clayton E LaBalle
*Assistant Examiner* — Leon W Rhodes, Jr.
(74) *Attorney, Agent, or Firm* — Young & Thompson

(57) ABSTRACT

A device for monitoring the freezing state of a biopharmaceutical fluid in a container intended to receive a biopharmaceutical fluid that must pass between the liquid state and the frozen state, includes a peripheral envelope (25) made of plastic, to be connected to a heat treatment receptacle (5), a sensor (19) suitable for detecting a control parameter which is a macroscopic parameter of the container, and an analysis system (62) suitable for determining a freezing state of the biopharmaceutical fluid on the basis of the macroscopic parameter of the container.

20 Claims, 9 Drawing Sheets

(51) Int. Cl.
*G01K 11/06* (2006.01)
*F25D 19/00* (2006.01)

(58) Field of Classification Search
USPC .......................................................... 374/24
See application file for complete search history.

(56) References Cited

U.S. PATENT DOCUMENTS

| | | | |
|---|---|---|---|
| 3,788,090 | A | 1/1974 | Richards |
| 3,838,794 | A | 10/1974 | Cogley et al. |
| 4,117,881 | A * | 10/1978 | Williams ............ A61M 1/0272 236/78 B |
| 5,163,909 | A | 11/1992 | Stewart |
| 5,399,166 | A | 3/1995 | Laing |
| 5,492,534 | A | 2/1996 | Athayde et al. |
| 5,505,708 | A | 4/1996 | Atkinson |
| 5,743,878 | A | 4/1998 | Ross et al. |
| 5,776,104 | A | 7/1998 | Guignard et al. |
| 5,799,830 | A | 9/1998 | Carroll et al. |
| 5,988,422 | A | 11/1999 | Vallot |
| 6,311,503 | B1 * | 11/2001 | Shapiro .................... F25C 1/10 62/138 |
| 6,453,683 | B1 * | 9/2002 | Wisniewski .............. F25C 1/04 62/135 |
| 6,499,838 | B2 | 12/2002 | Seccombe et al. |
| 2004/0232171 | A1 | 11/2004 | Bobst |
| 2009/0075362 | A1 | 3/2009 | Baumfalk et al. |
| 2009/0202978 | A1 * | 8/2009 | Shaham ................... A01N 1/02 435/1.3 |
| 2011/0120151 | A1 | 5/2011 | Cutting et al. |
| 2011/0120667 | A1 | 5/2011 | Cutting |
| 2012/0102982 | A1 | 5/2012 | Zhou et al. |

FOREIGN PATENT DOCUMENTS

| | | |
|---|---|---|
| EP | 1 407 302 A1 | 4/2004 |
| EP | 1 475 112 A1 | 11/2004 |
| EP | 1 441 585 B1 | 5/2006 |
| EP | 1 441 586 B1 | 6/2006 |
| EP | 1 389 292 B1 | 10/2008 |
| EP | 2 101 129 A3 | 9/2009 |
| EP | 2 113 171 A2 | 11/2009 |
| EP | 1 407 202 B1 | 1/2010 |
| FR | 2 682 602 A1 | 4/1993 |
| JP | H01-159576 A | 6/1989 |
| JP | 2000-44939 A | 2/2000 |
| WO | 94/27659 A1 | 12/1994 |
| WO | 00/04131 A1 | 1/2000 |
| WO | 02/099487 A1 | 12/2002 |
| WO | 2007/103917 A2 | 9/2007 |
| WO | 2011/063381 A2 | 5/2011 |
| WO | 2012/037535 A2 | 3/2012 |
| WO | 2012/044403 A1 | 4/2012 |

OTHER PUBLICATIONS

International Search Report, dated May 9, 2014, from corresponding PCT Application.
Chinese Office Action issued in Application No. 201480025322.X, dated Apr. 12, 2017.
European Office Action issued in Application No. 14 711 255.1, dated Feb. 22, 2017.
European Notification according to Article 94 (3) EPC dated Jul. 19, 2016; Application No. 14711254.4.
China Office Action dated Jul. 12, 2016; Application No. 201480025049.0.

* cited by examiner

MONITORING OF THE FREEZING STATE OF A BIOPHARMACEUTICAL FLUID FOUND IN A CONTAINER

TECHNICAL FIELD

The invention concerns the monitoring of the freezing state of a biopharmaceutical fluid located in a container.

It relates to a container adapted to receive a biopharmaceutical fluid, specially equipped for monitoring the freezing state of the biopharmaceutical fluid, a system including such a container and a device for monitoring the freezing state of the biopharmaceutical fluid, and a method for monitoring the freezing state of the biopharmaceutical fluid located in such a container.

BACKGROUND OF THE INVENTION

In the context of the invention, the term "biopharmaceutical fluid" is understood to mean a fluid derived from biotechnology—culture media, cell cultures, buffer solutions, artificial nutrition liquids, blood fractions and derivatives of blood products, or a pharmaceutical fluid or more generally a fluid for use in the medical field.

A container having a flexible peripheral wall, specially adapted to receive such a biopharmaceutical fluid, is already known and is quite satisfactory. Generally, such a container may be associated with a rigid support structure to form a biopharmaceutical fluid containing means. Such a containing means is described for example in EP 1,441,585. Further examples of such containing means can be found in WO 2007/103917.

To better preserve a biopharmaceutical fluid before a process step or for later use, it has also been proposed to keep it in frozen form. Thermal treatment systems (heat and/or cold) have been provided for this purpose, in particular for freezing the biopharmaceutical fluid contained in the containers. The specific properties of biopharmaceutical fluids have led to the development of containers specially adapted for freezing, for example having a slightly flared shape as described in EP 1,441,586.

Similarly, freezing systems have recently been provided that are specially adapted for biopharmaceutical fluids. Such a system is described in EP 1,389,292 for example, and is particularly effective. EP 1,407,302 describes another system that is particularly suitable for trapezoidal containers. Recently, an improved freezing system for bags was disclosed in WO 2011/063381.

It is understood that for biopharmaceutical fluids it is absolutely critical to monitor and control the freezing state. Incorrectly controlled freezing can lead to deterioration or total loss of the biopharmaceutical fluid. Moreover, for economic reasons, the freezing process should not be slowed too much. In order to have more information about the freezing process, containers to be thermally treated have begun to be equipped with temperature sensors.

Such sensors offer the advantage of obtaining information from inside the container. This is not a perfect solution, however. First, such a sensor is intrusively placed inside the container. It is therefore necessary to create it of materials that do not affect the biopharmaceutical fluid, and to have it communicate with the outside world in a manner that does not contaminate the container contents, which may require attaching it through the container wall in a fluidtight and sterile manner.

Moreover, such a sensor only provides localized information, limited to the location where it is placed. As long as the fluid is predominantly in a liquid state, natural convection movements within the container or locational inconsistencies in the thermal treatment may go unreported by these localized sensors. In addition, once the portion of the biopharmaceutical fluid where the sensor is located has solidified during the freezing process, no further information will be available from this sensor aside from information for its precise location. The beginning of the thawing process will also be very difficult to monitor with such an approach.

One solution might be to increase the number of sensors. However, aside from the intrusion and sterility problems mentioned above, the cost of such a system will increase proportionately with the volume of the container, which is not acceptable.

To overcome this problem, WO 2012/044403 recently proposed monitoring the evolution of the freezing front by ultrasound imaging. Although this system is very promising, there is current need for an alternative system that is simple, inexpensive, and non-intrusive.

SUMMARY OF THE INVENTION

A description of the invention as characterized in the claims is presented below.

In a first aspect, the invention relates to a device for monitoring the freezing state of a biopharmaceutical fluid in a container intended to receive a biopharmaceutical fluid that is to transition between the liquid state and the frozen state. The container comprises a peripheral envelope made of plastic, intended and suitable for association with a freezing receptacle.

The device for monitoring the freezing state comprises a sensor suitable for detecting a control parameter which is a macroscopic parameter of the container, and an analysis system suitable for determining a freezing state of the biopharmaceutical fluid on the basis of the macroscopic parameter of the container.

A "macroscopic" parameter of the container is understood to mean a parameter relating to the container as a whole, as opposed to a parameter relating to a specific localized area of the container which is typically the case for data provided by a temperature sensor. Various non-limiting examples of macroscopic parameters will be given below. For example, these can be the volume of the container, if this is variable, or the gas pressure in the container, if this is variable, or a corollary parameter of these.

Surprisingly, it was found that information could be obtained on the freezing state of the biopharmaceutical fluid within the container by monitoring a parameter of the container as a whole, regardless of the container size. The above system is thus suitable for small containers (a few centiliters or less) as well as for large containers (one hundred or several hundred liters at least). In addition, this system is as effective for freezing operations as it is for thawing operations.

In one embodiment, the sensor is adapted to detect a value of the control parameter repeatedly over time during the thermal treatment process.

In one embodiment, the parameter values over time show an abrupt change when there is a change in the freezing state of the biopharmaceutical fluid, and the analysis system is adapted to detect this abrupt change.

In one embodiment, the parameter values over time show an abrupt change when transitioning between a state where a portion of the biopharmaceutical fluid is not frozen and a state where the entire biopharmaceutical fluid is frozen.

In one embodiment, the parameter values over time show an abrupt change when transitioning between a state where the entire biopharmaceutical fluid is not frozen and a state where a portion of the biopharmaceutical fluid is frozen.

In one embodiment, the analysis system is adapted to determine a frozen state of the biopharmaceutical fluid on the basis of an absolute value of the control parameter.

In one embodiment, the analysis system is adapted to determine the frozen state of the biopharmaceutical fluid on the basis of an initial value of the control parameter and of a change over time in the absolute value of the control parameter determined from the sensor.

In one embodiment, the control parameter is representative of an average density of the non-gaseous phases of the biopharmaceutical fluid contained in the container.

In one embodiment, the non-gaseous phases comprise one and/or the other among a liquid phase and a solid phase, the container possibly further containing a gaseous phase.

In one embodiment, the control parameter is the gas pressure in an upper portion of the container arranged above the biopharmaceutical fluid in an end head portion of the container, said portion being filled with gas.

In one embodiment, the monitoring device comprises a gas entry/exit line adapted to be associated in a fluidtight communication with a gas entry/exit port of the container, said port being located in an upper portion of the container arranged above the biopharmaceutical fluid in an end head portion of the container, said portion being filled with gas, the sensor being suitable for determining a parameter of the headspace.

In one embodiment, the control parameter is the amount of gas in the headspace, the volume of gas in the headspace, or the volume of biopharmaceutical fluid in the container.

In one embodiment, the monitoring device further comprises an opening/closing valve associated with the gas entry/exit port.

In one embodiment, the sensor comprises a pressure sensor intended and suitable for measuring or monitoring the gas pressure in the upper portion or in the gas entry/exit line, and a regulation system intended and suitable for controlling the entry/release of gas into/from the upper portion via the gas entry/exit port (30) and the gas entry/exit line, according to a desired pressure profile in the headspace.

In one embodiment, the monitoring device further comprises a means intended and suitable for allowing the entry/release of gas into/from the headspace, via the gas entry/exit port and the gas entry/exit line.

In one embodiment, the regulation system intended and suitable for controlling the entry/release of gas into/from the upper portion, via the gas entry/exit port and the gas entry/exit line, operates so as to allow the entry of gas when the gas pressure in the upper portion decreases and to release gas when the gas pressure in the upper portion increases.

In one embodiment, the monitoring device further comprises a control system suitable for thermally controlling the freezing receptacle according to the freezing state determined by the analysis system.

In another aspect, the invention relates to a thermal treatment system for a biopharmaceutical fluid, comprising a thermal treatment receptacle intended and suitable for receiving a container of biopharmaceutical fluid, and such a monitoring device.

In one embodiment, the thermal treatment system comprises a plurality of thermal applicators in the receptacle, independently controllable, and the control system independently controls said thermal applicators.

In one embodiment, the system comprises a plurality of thermal treatment receptacles each intended and suitable for receiving a respective container of biopharmaceutical fluid, each receptacle being independently controllable by the control system, the control system being adapted to control each thermal treatment receptacle independently according to the freezing state determined for each container.

In another aspect, the invention relates to a method for monitoring the freezing state of a biopharmaceutical fluid in a container intended to receive a biopharmaceutical fluid that is to transition between the liquid state and the frozen state, comprising a peripheral envelope made of plastic, intended and suitable for association with a thermal treatment receptacle, characterized in that a sensor detects a control parameter which is a macroscopic parameter of the container, and an analysis system determines a freezing state of the biopharmaceutical fluid on the basis of the macroscopic parameter of the container.

BRIEF DESCRIPTION OF THE DRAWINGS

The drawings in the figures will now be briefly described.

Below is a detailed description of several embodiments of the invention, with examples and with reference to the drawings.

DETAILED DESCRIPTION

Figure 1:
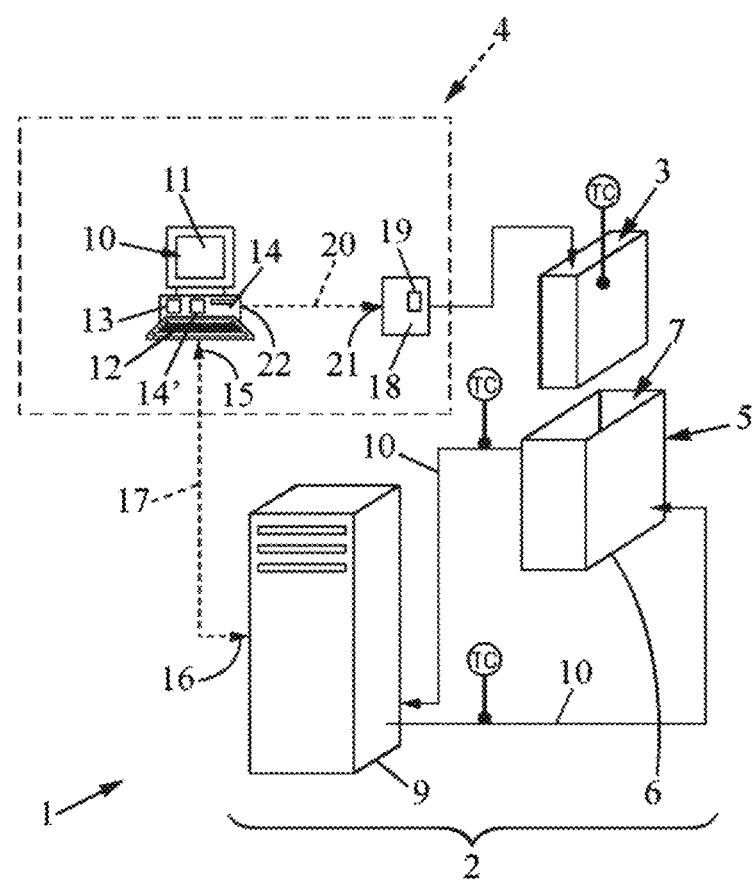
FIG. 1 is a schematic view representing a thermal treatment system for biopharmaceutical fluid.

The invention relates to a thermal treatment system 1 for a biopharmaceutical fluid, of which one example is shown in FIG. 1. A thermal treatment system 1 comprises a thermal treatment station 2 adapted to apply a thermal treatment to a containing means 3 for biopharmaceutical fluid, and a monitoring device 4.

As can be seen in FIG. 1, the thermal treatment station 2 may comprise a thermal treatment receptacle 5 comprising a body 6 defining a cavity 7 of suitable shape for receiving a biopharmaceutical fluid containing means 3 of suitable shape. The thermal treatment station may, for example, operate by thermal conduction between the body 6 and the biopharmaceutical fluid containing means 3. In such an example, the body 6 supports one or more applicator elements 8 which are placed in direct or indirect contact with the biopharmaceutical fluid containing means 3 when the latter is introduced into the cavity. Examples of applicator elements will be described below. The applicator element or elements 8 apply a thermal field in the cavity 7, for example by direct or indirect contact with the biopharmaceutical fluid containing means 3.

The thermal treatment station 2 also comprises a thermal generator 9, adapted to generate heat and/or cold on command. The thermal generator 9 is connected to the applicator elements 8 by a carrier line 10, allowing the thermal generator 9 to modify the temperature of the applicator elements 8. Depending on the applications, the thermal generator may be a cold-generating device, a heat-generating device, or a combination of these two devices.

The monitoring device 4 may comprise multiple units placed together at one station or distributed. The monitoring device may include a user interface 10 (for example a screen 11, mouse, keyboard 12, etc.) allowing a user to interact with the thermal treatment station 2. Such interaction includes, for example, displaying on the screen 11 the temperature data applied by the thermal generator 9. The monitoring device 13 may therefore comprise a memory 13 that stores temperature data, and a processor 14 to process these data for display on the screen 11, for example as a graph or alphanumeric values. The monitoring device 4 also comprises a communication interface 15 to communicate with a communication interface 16 of the thermal generator 9. A communication line 17 exists between the communication interfaces 15 and 16. This line may be wired or wireless.

Thus, according to this first example, the applied temperature data are transmitted from the thermal generator 9 to the monitoring device 4 via this communication line 17.

A second example of interaction between the monitoring device 4 and the thermal treatment station 2 can concern the control of the thermal treatment station 2 by the monitoring device 4. For example, a control system 14' of the processor 14 of the monitoring device 4 sends the thermal generator 9 a temperature profile to be applied. This profile may be a target temperature, a temperature profile over time, or some other profile.

This temperature profile may be entered into the monitoring device by a user, for example using an input interface (keyboard 12), or loaded from memory 13 of the monitoring device 4, possibly removable (USB key, CD, etc.).

The monitoring device 4 also comprises instrumentation 18. The instrumentation 18 will be described in more detail below. Here we can simply state that this instrumentation 18 includes a sensor 19 adapted to measure a macroscopic parameter of a container of the biopharmaceutical fluid containing means 3, and a communication line 20 adapted to transmit detection data obtained by the sensor 19 to the memory 13 of the monitoring device 4 for further processing. Similarly to communication line 17, communication line 20 may be wired or wireless, and extends from a first communication interface 21 associated with the sensor 19 to a second communication interface 22 associated with the processor 14.

Figure 2:
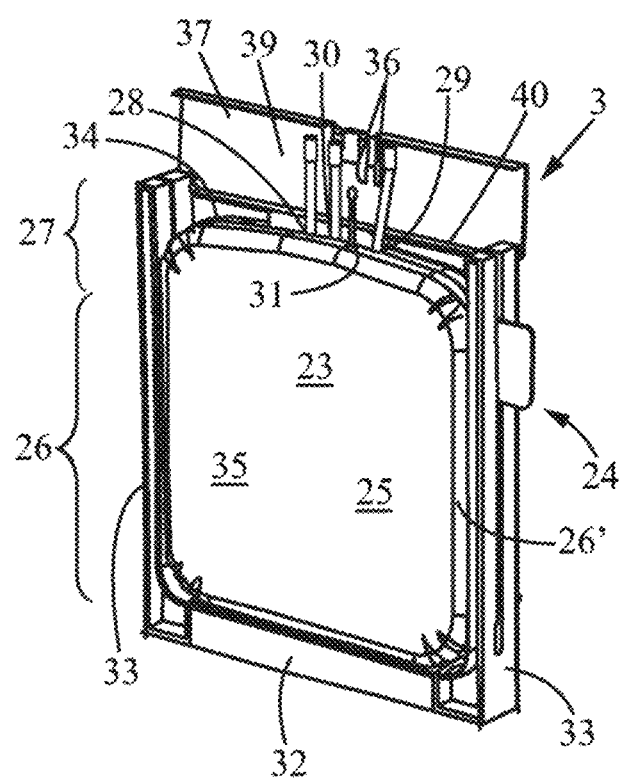
FIG. 2 is a perspective view representing a biopharmaceutical fluid containing means according to a first embodiment, suitable for the system of FIG. 1.

We will now refer more specifically to FIG. 2, illustrating a containing means 3 for biopharmaceutical use having a flexible container 23 filled with content, namely a biopharmaceutical product which in general is liquid or pasty, received and externally supported in a rigid receiving and support structure 24. Either the content is always liquid or pasty, or it is at some point or during a particular period. For example, the content can be in a solid state as a result of a freezing process, or in a fluid state after thawing.

Here, "biopharmaceutical product" is understood to mean a product derived from biotechnology—culture media, cell cultures, buffer solutions, artificial nutrition liquids, or a pharmaceutical product or more generally a product intended for use in the medical field. The biopharmaceutical product is liquid or pasty as a whole, at least when it is to be mixed, so as to allow it to be mixed. It may only have one fluid phase or several, including products that are originally solid or have a certain solidity, for mixing with a fluid medium. Such a containing means 3 is typically intended for the preparation of a biopharmaceutical product, for storage, for transport, or for carrying out a certain process of physical, chemical, or biological nature such as mixing, or bioreactor or system for freezing/thawing.

The flexible container 23 comprises a flexible envelope 25 which defines an interior space capable of receiving the content and here having actually received it.

Such a container 23 is typically a 3D bag comprising two main walls interconnected by and welded to two side gussets, which can be folded flat (particularly for storage and transportation) or unfolded and deployed (for filling with content), the volume of the interior space possibly being at least 50 liters, up to 3,000 liters or more. Such a 3D bag is described in WO00/04131A1 or is commercially available under the brand FLEXEL® 3D. It is understood that this bag embodiment is provided as a purely illustrative example, and that the flexible container can be implemented differently. The principles of the arrangement and construction of such a flexible container 23 are part of the general knowledge or are within the reach of the skilled person. In all cases, the container 23 has a certain flexibility, being made of a plastic film having a certain flexibility, of a single layer or most often of multiple layers. To ensure the external support of such a flexible container 23 of large volume, once filled with content, it is placed in and externally supported by the rigid receiving and support structure 24.

The flexible container 23, when filled and in position, has a horizontally arranged lower portion 26, a peripheral side portion 26', and an upper portion 27 that is also arranged horizontally. It also presents a substantially vertical main axis AA, relative to which the terms "lower," "upper," "side," "horizontal," and "vertical" are applied to the flexible container as a whole. Due to gravity, the fluid, liquid, pasty, or partially solid content will be located primarily in the lower portion 26 of the flexible container 23 during the thermal treatment, while the upper portion 27 will primarily contain a gas at pressure P.

The flexible container 23 is usually provided with ports, for example such as an entry port 28 for admitting or introducing a product to be mixed with the content of the container 23, located in the upper portion 27 of the flexible container 2, an exit port 29 for discharging the mixed product from the container 23, a gas feed port 30, and where appropriate a port 31 for mounting a functional device or measurement means, for example for measuring a parameter indicative of or related to the homogeneity, the heterogeneity, or the blending of the content in the interior space.

For example, such measurement means are light-sensitive and measure the transparency or opacity or homogeneity or heterogeneity of the content of the flexible container 23 or the mixing time of its content. The principles of the arrangement of such ports 28-31 are part of the general knowledge of or are within the reach of the skilled person. The four ports are, for example, arranged in the upper portion 27 of the container, with the exit port 29 then being connected to the bottom of the flexible container 23 inside the latter by an internal tube (not shown). The gas feed port 30 is preferably in communication with the upper portion 27 of the flexible container 23 containing gas.

The rigid receiving and support structure 24 typically comprises, as shown here, a lower bottom wall 32, arranged horizontally, and a side wall 33, arranged vertically, and an opening 34 in the upper portion for the insertion and removal of the flexible container 23. The rigid receiving and support structure 24 defines an interior space 35 accessible through the opening 34. This space 35 receives and externally supports the flexible container 23 such that the lower portion 26 and side portion 26' of its flexible envelope 25 press against the inside face of the bottom wall 32 and side wall 33. In addition, the rigid receiving and support structure 24 is usually provided with holes 36 which can cooperate with the ports of the flexible container 23. Where appropriate, the rigid receiving and support structure 24 also comprises restraining means 37 suitable for being applied against the upper portion 27 of the flexible container 23.

The restraining means 37 may, for example, comprise a restraining flap 39 pivoting on the side walls 33 by means of a hinge 40, between an open position shown in FIG. 2 and a closed position where the flap 39 extends substantially horizontally and is locked to retain the container 23 within the interior space 35. The flap 39 comprises slots including the holes 36 providing access to the ports 28-31.

The principles of the layout and implementation of such a rigid receiving and support assembly 3 are part of the general knowledge of or are within the reach of the skilled person. In all cases, the rigid receiving and support structure 24 is rigid and constitutes a fixed, non-deformable part supporting the flexible container 23. Of course, the rigid receiving and retaining assembly 3 can be transported and possibly disassembled or folded.

Alternatively, there may not be such a rigid structure 24. This can be the case for the more easily manipulated containers of small dimensions, holding several liters (about 1-5 liters).

Figure 3:
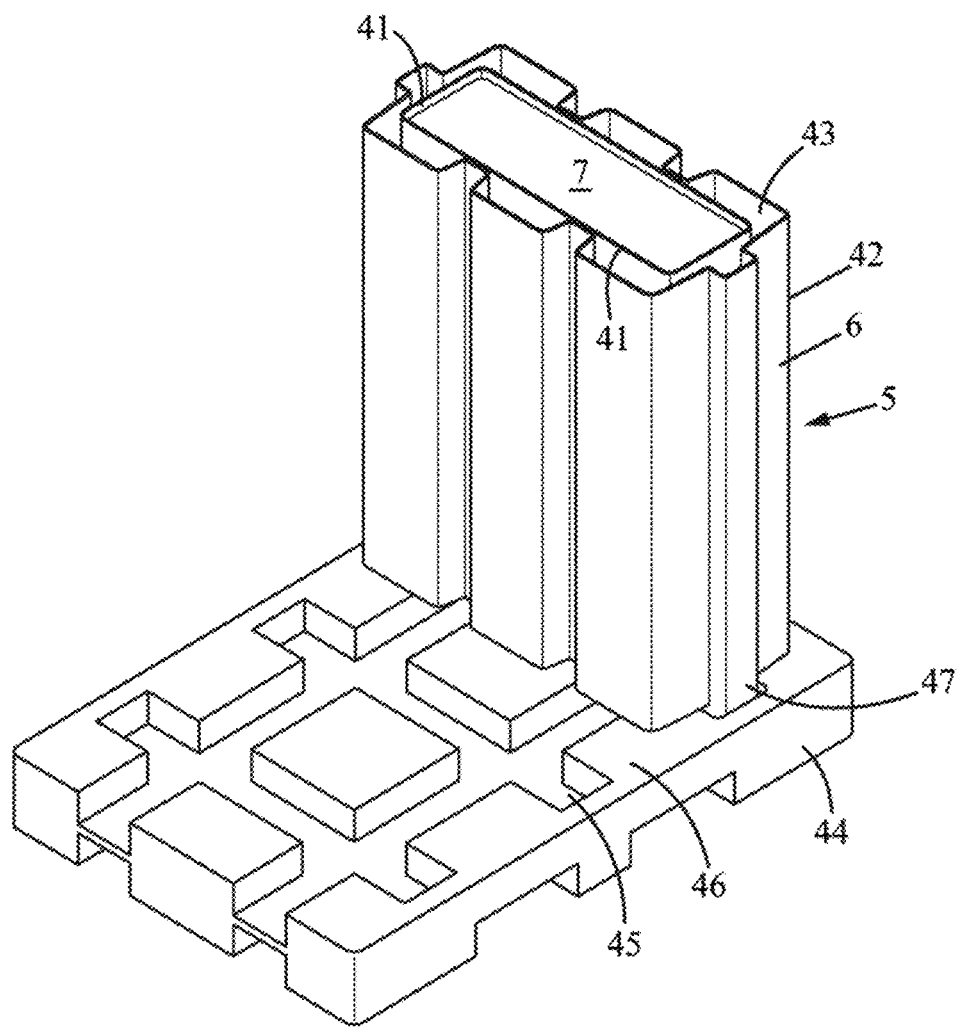
FIG. 3 is a schematic partial perspective view of a portion of a thermal treatment system.

FIG. 3 shows a receptacle 5 specially adapted to receive a biopharmaceutical fluid containing means as described above. The receptacle 5 comprises a body 6 defining a so cavity 7. The body 6 comprises an inner wall 41 extending from an open upper end to a lower base. The inner wall 41 defines a contact surface for the containing means 3. The body 6 also comprises an outer wall 42 extending downward from an upper end at the upper end of the inner wall 41. The inner wall 41 and outer wall 42 define between them a plurality of pockets 43, which are cavities extending between the inner wall 41 and outer wall 42 from top to bottom. It may be arranged, for example, that the inner wall 41 is substantially flat on each longitudinal side of the cavity 7, and that on this same side, the outer wall has a regular slotted profile, two slots together with the inner wall 41 defining a pocket 43.

The thermal treatment station 2 may further comprise a stand 44 on which the receptacle 5 is placed. Mechanical retention of the receptacle 5 on the stand 44 may be provided for example. For example, the receptacle 5 and the stand 44 have complementary shapes that cooperate. In the example shown, the stand 44 comprises a groove 45 in its upper face 46. The receptacle 5 comprises a projecting portion 47 inserted into the groove 45. For example, the projecting portion 47 is provided on each narrow side face of the outer wall 42. Thus, the projecting portions 47 are inserted into the grooves 45 formed in the upper face 46 of the stand 47, and the bottom of the pockets 43 rests on this upper face 46.

Figure 4:
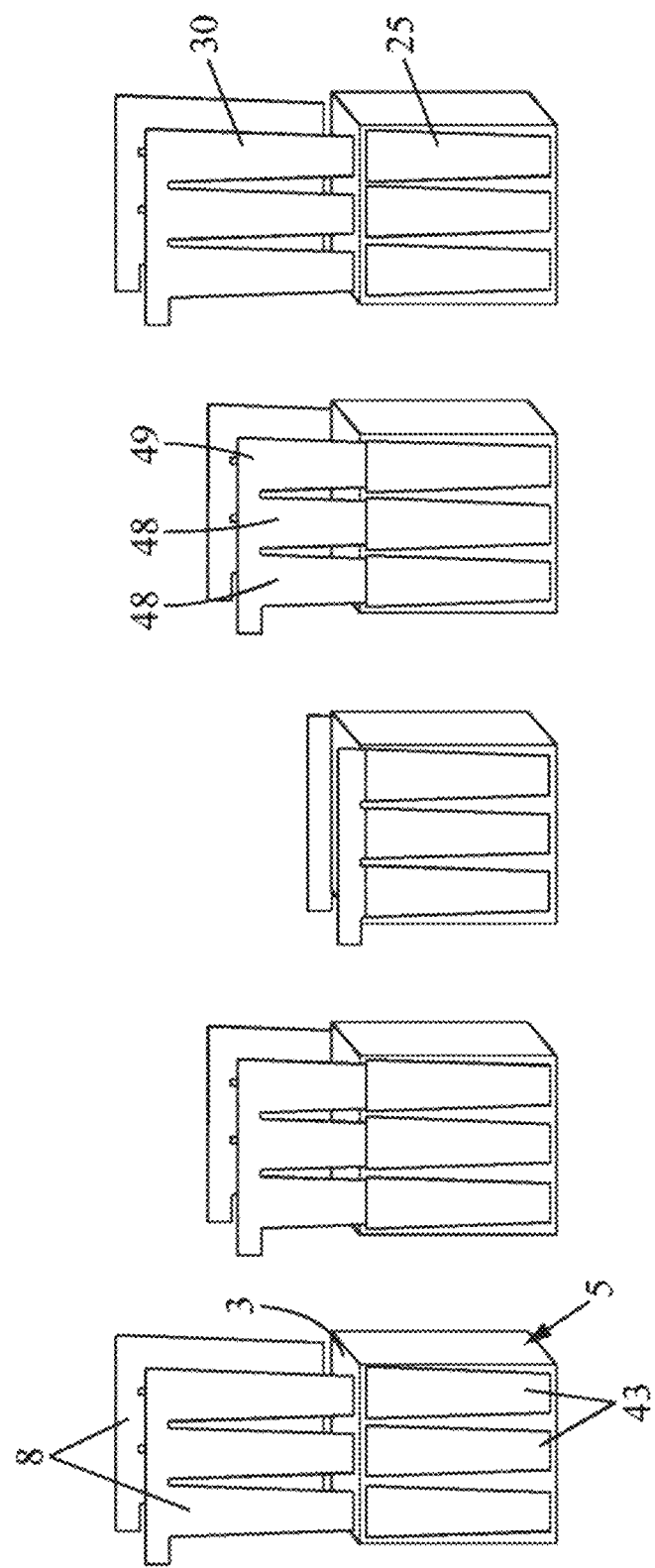
FIG. 4 is a set of side views representative of an exemplary thermal treatment process for biopharmaceutical fluid that is based on the system of FIG. 3.

An exemplary thermal treatment process is now described with reference to FIG. 4. First, the containing means 3 is placed in the receptacle 5. Then, the containing means 3 is thermally treated by means of applicator elements 8. In the present example, two applicator elements are used, each associated with a respective wide side of the receptacle 5. Each applicator element 8 comprises a plurality of parallel cooling fingers 48, each entering a respective pocket 43 of the receptacle 5. The fingers 48 of an applicator element 8 are connected together and to the outside via a distributor 49. The distributor 49 is connected to the thermal generator 9, to apply the thermal treatment to the containing means 3. The thermal treatment (for example heating or cooling, freezing or thawing) is then applied to the containing means 3 via the inner wall 41.

After a certain amount of time, once the thermal treatment is complete, the applicator elements 8 can be withdrawn in a manner that reverses their insertion.

Figures 5A, 5B:
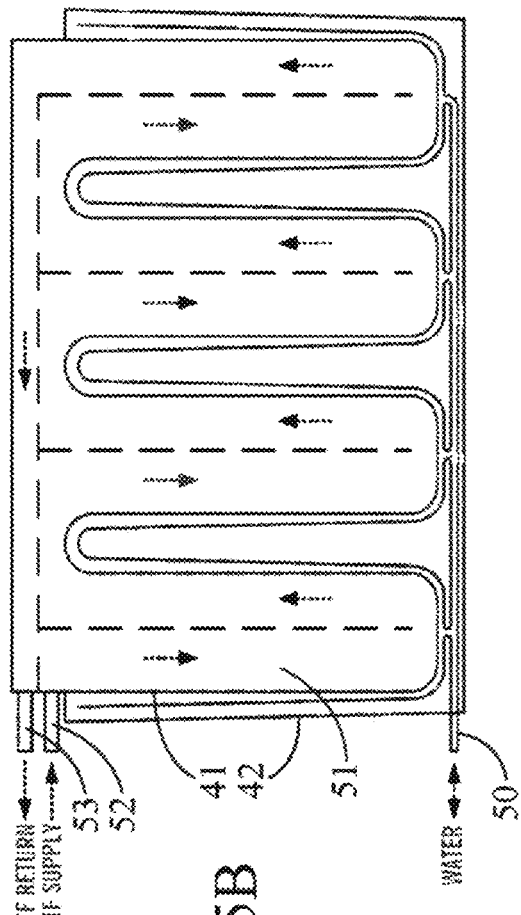
FIGS. 5a and 5b are respectively top and side views of the system of FIG. 3.

As can be seen in FIG. 5b, it may be arranged that the pockets 43 are prefilled with a fluid to improve the heat transfer between the applicator element 8 and the inner wall 41 of the body 6. Such a fluid may be water for example. Space is left to allow the applicator elements 8 to enter the pockets 43, but this space is filled with a fluid enabling good temperature transfer. Thus, the bottom of the receptacle 5 is provided with a feed line 50 for this transfer fluid, and suitable for filling the bottom of each pocket 43.

Furthermore, each applicator element 8 comprises an internal pipe 51 allowing the circulation of a thermal treatment fluid. The internal pipe 51 extends for example from an inlet 52 to an outlet 53 which are arranged side by side, and snakes through the cooling fingers 48 of an applicator element. The thermal treatment fluid enters via inlet 52, from the thermal generator 9.

Figure 6:
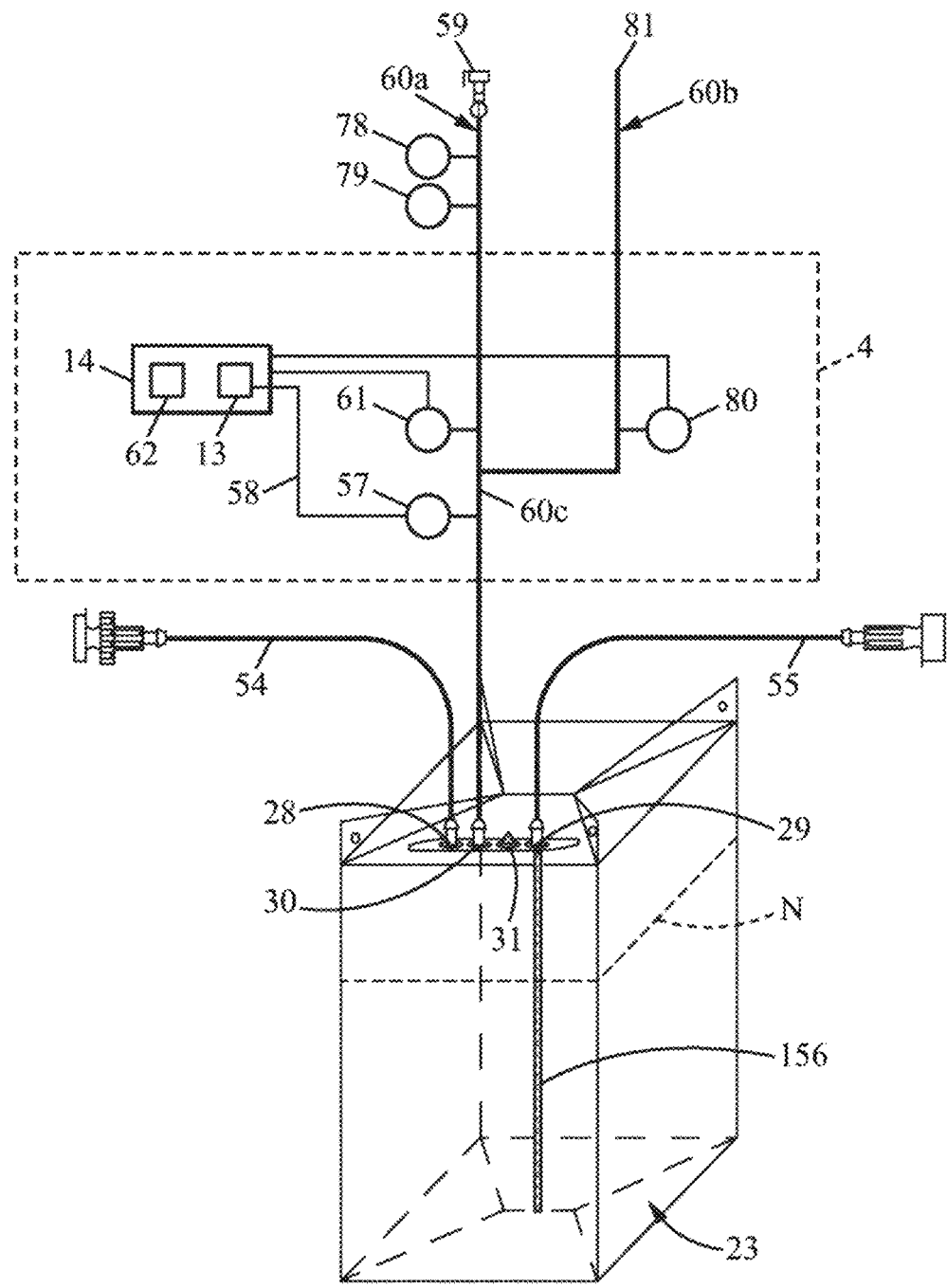
FIG. 6 is a schematic perspective view of a portion of a thermal treatment system according to a second embodiment.

FIG. 6 schematically shows the container 23 of biopharmaceutical fluid and a device 4 for controlling the freezing state of the biopharmaceutical fluid contained in the container 23. The system may also comprise a filling line 54 in fluidtight fluid communication with the entry port 28 of the container 23, for delivering biopharmaceutical fluid into the container 23. The system may comprise a discharge line 55 in fluidtight fluid communication with the exit port 29 of the container 23, for delivering biopharmaceutical fluid from the container 23. In this figure, the tubing 156 internal to the container 23 and connecting the exit port 29 to the bottom of the container 23 is represented.

The monitoring device 4 also comprises a sensor adapted to detect a macroscopic parameter of the container 23. Generally, the macroscopic parameter is derived directly or indirectly from the average density of the non-gaseous portion of the content of the container 23.

A first example will be described below.

In this first example, the container 23 is only partially filled with biopharmaceutical fluid, and the level of fluid in the container is schematically represented by a horizontal dotted line N in FIG. 6. The upper head portion of the container 23 (above the dotted line) is therefore filled with gas.

In this first example, the pressure P of the gas contained in the container 23 is regulated by a pressure regulation system. One can, for example, use a system such as those used for verifying filter quality. Regulating the pressure inside the container 23 prevents the gas pressure from exceeding a predetermined limit that could affect the physical integrity of the container. In addition, the fact that the pressure is maintained above a certain limit ensures that there is physical contact between the upper portion of the container 23 and the inner wall 41 of the thermal treatment system. Thus, the pressure control system firstly comprises a pressure sensor 57. In one example, the pressure sensor 57 is positioned at a location in fluid communication with the interior of the container 23, and is adapted to detect the gas pressure in the upper head portion of the container 23. For example, the pressure sensor 57 is located in the gas entry/exit line 60. The pressure sensor 57 regularly sends measured pressure data to the memory 13 of the processor 14. It may be arranged, for example, to have a wired transmission line 58 running from the pressure sensor 57 to the processor 14. The pressure sensor 57 detects a control parameter which is a macroscopic parameter of the container 23, which means considering the flexible container 23 as a whole. The pressure in the headspace of the container depends on the state of the container as a whole, and not just the location where the pressure sensor 57 is positioned.

The gas entry/exit line 60 comprises a gas infeed section 60a, a gas outfeed section 60b parallel to the gas infeed section 60a, and a common section 60c which is connected at one end to the gas infeed 60a and gas outfeed 60b sections, and is connected at the other end to the gas entry/exit port 30. The pressure sensor 57 is placed to allow detecting the gas pressure in the common section 60c. The pressure regulation system also comprises a gas source 59 in fluid connection with the gas infeed section 60a. The gas infeed section 60a may have a pressure sensor 78 and a controller 79 which are adapted to regulate the pressure of the gas released from the gas source 59 to the common section 60c of the gas entry/exit line 60. There is also provided an inlet valve 61 on the gas infeed section 60a of the line 60, between the source 59 and gas entry port 30. The inlet valve 61 is controlled by the processor 14 according to the pressure data detected by the pressure sensor 57, to alternate between allowing the entry of gas from the source 59 to inside the container 23 and preventing such entry. The gas in question is, for example, air or nitrogen ($N_2$). There is also provided an outlet valve 80 on the gas outfeed section 60b of the line 60, between the common section 60c and an outlet 81 to the outside. The outlet valve 80 is controlled by the processor 14 according to the pressure data detected by the pressure sensor 57, to alternate between releasing gas from the container 23 or preventing such release.

In one particular example, it can be arranged that a target pressure profile for the pressure data measured within the flexible container 23 is defined. For example, a desired pressure profile is defined, constant at a given value such as 100 millibar (mbar) for example. In practice, an upper limit value and a lower limit value are defined. The pressure is considered to be constant if these two values are close compared to the absolute value of one of them (for example the difference between the two limit values is less than 10% of the upper limit value). A closing pressure between these two limit values is also defined. Alternatively, two distinct closing pressures may be defined, one associated with and greater than the lower limit value, and the other associated with and less than the upper limit value.

Thus, if the detected pressure is greater than this upper limit value, the outlet valve 80 is opened by the processor 14 and the excess gas is free to escape, until the pressure in the container 23 reaches the closing pressure. If the detected pressure is less than this lower limit value, the inlet valve 61 is opened by the processor 14, and the gas from the source is allowed to enter the container 23 until the pressure in the container 23 reaches the closing pressure.

In this exemplary embodiment, the processor 14 comprises an analysis system 62 adapted to determine the frozen state of the fluid contained in the containing means. In this first example, the analysis system 62 comprises an analyzer of the pressure data detected by the pressure sensor 57 over time.

Figure 7:
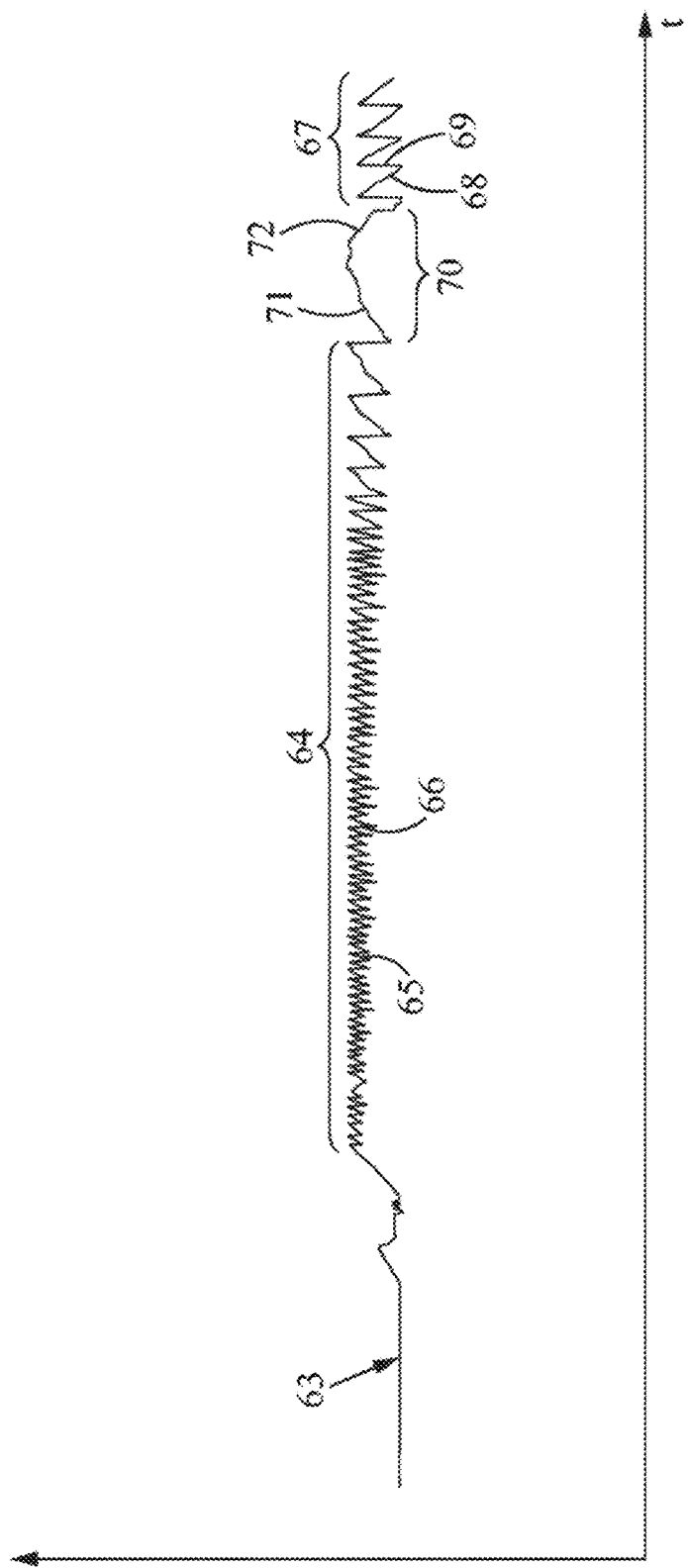
FIG. 7 is a graph illustrating an exemplary implementation of the system of the preceding figures.

In this exemplary embodiment, FIG. 7 represents a graph 63 of the pressure over time, as detected by the pressure sensor 57 during an operation of freezing the biopharmaceutical fluid, in the case described above where a constant gas pressure is maintained in the container 23. During a first portion 64 of the freezing step, the initially liquid fluid gradually solidifies. As is generally known, this step is accompanied by an increase in the volume of the biopharmaceutical fluid in the container 23, because its density in solid form is lower than its density in liquid form. This increase in volume is accompanied by a compression of the gas in the container headspace 23. The progressive compression of the gas can be seen, in the first portion 64 of the curve, as a segment 65 of the curve sloping diagonally from a lower left point to an upper right point (pressure increase measured over time). Because the pressure is regulated to maintain a constant pressure, when the pressure increase described above becomes greater than an upper limit value, the processor 14 causes the outlet valve 80 to open, and gas is released from the headspace of the container 23. The sudden drop in the gas pressure due to the opening of the outlet valve 80 can be seen in the first portion 64 of the curve, as a segment 66 of the curve sloping diagonally from an upper left point to a lower right point (pressure drop measured over time). The outlet valve 80 remains open until the measured pressure returns to below a limit value, at which point the processor 14 causes the outlet valve 80 to close. The pressure drops sharply while it is open, which can be seen by the fact that absolute value of the slope of segment 66 is much greater than that of the slope of segment 65.

The above phenomenon is repeated as long as the liquid biopharmaceutical fluid is changing to a solid state.

Let us assume that all the biopharmaceutical fluid contained in the container 23 is frozen solid. Continuing the cooling results in increased density of the solid and consequently a drop in the volume of the biopharmaceutical fluid contained in the container. This decrease in volume results in an increase in the volume of the upper headspace. This increase in volume tends to reduce the pressure measured in the upper headspace of the container 23. A gradual pressure decrease of the gas can be seen in a second portion 67 of the curve, as a segment 68 of the curve sloping diagonally from an upper left point to a bottom right point (pressure drop measured over time). As the pressure is maintained at a constant pressure, when the pressure drop described above falls below a limit value, the processor 14 causes the inlet valve 61 to open and thus to allow gas to flow from the cylinder 59 to the container 23 headspace. The sudden gas pressure increase due to the opening of the inlet valve 61 can be seen in the second portion 67 of the curve, as a segment 69 of the curve sloping diagonally from a lower left point to an upper right point (pressure increase measured over time). The inlet valve 61 remains open until the measured pressure returns to above a limit value, at which time the processor 14 causes the inlet valve 61 to close. 3o The pressure drops sharply while it is open, which can be seen by the fact that the absolute value of the slope of segment 69 is much greater than that of the slope of segment 68.

Thus, during a freezing phase, the outlet valve 80 allows the release of gas. Once the freezing is complete, the inlet valve 61 allows the entry of gas. Detection of the transition between these two states thus indicates completion of the freezing phase. The phenomenon of increasing density of the solid only begins to occur once the transition to the solid phase is entirely complete.

As is particularly visible in FIG. 7, detection of the transition between the two states is indicated by an intermediate portion 70 of the graph of pressure over time, located between the two portions 64 and 67. In this intermediate portion 70, the graph of pressure over time does not resemble the pattern in portions 64 or 67. In fact, the pressure first increases in a first area 71 without reaching the upper limit value, then decreases in a second area 72 until it reaches the lower limit value.

A data analyzer in the analysis system 62 of the processor 14 is quite able to identify in which of the portions 64, 67, or 70 is located a series of data measured during a short interval of time. For example, the analysis system only needs to compare the shape of a graph portion representative of the data present between two minima, with the graph portion between the two previous minima, to determine in which graph portion the system is. Alternatively, it may be sufficient to calculate the time difference between two successive minima as a function of time, and determine a maximum of this new variable, to determine at what point the entire biopharmaceutical fluid is frozen.

Thus, the above system can be used to determine, in a purely qualitative manner, the freezing state of a biopharmaceutical fluid among the states of "not fully frozen", "end of freezing", and "fully frozen", by simply monitoring the evolution of the pressure values over time or the values obtained from these pressure values, and by watching for a particular pattern. This determination can be done regardless of the size of the container 23 by monitoring a single macroscopic parameter indicative of the state of the container.

The above method may require knowing the state of the biopharmaceutical fluid at the start of the thermal treatment process (but this is generally known). The state of the biopharmaceutical fluid at the start of the thermal treatment process can, however, be determined by the system by analyzing the first portion of the pressure data as a function of time. This parameter therefore does not have to be entered into the processor 14 by the user.

The system described above has been described for the case of pressure regulated at a constant pressure, meaning between a maximum limit and a minimum limit which are close on the pressure value scale. Alternatively, however, one could use any pressure profile.

The method described above does not need to know the absolute value of the measured pressure, but simply needs to monitor the evolution of this value over time.

Alternatively, the pressure measurement is not used directly, but simply data representative of the signal indicating the opening of valve 61 and/or valve 80 over time. These data can be represented by a binary curve with a succession of 1 states over time, separated by 0 states. Thus, the longest 0 state can correspond to the end of the freezing process. The control parameter may be a binary parameter relating to whether or not one or two valves of a controlled pressure system is (are) open. In such a method, it may be useful for the system to know the initial state of the biopharmaceutical fluid contained in the container 23. The user can use the interface 12 to enter into the memory 14 a parameter indicating the initial state of the fluid.

Alternatively, there could be a single valve operating in both directions, replacing the paired inlet valve 61 and outlet valve 80. Such a bidirectional valve can be provided on the common section 60c. If the single valve provides a signal having a different sign according to the direction it is open (direction the gas travels), the freezing state of the fluid can be obtained directly from data representative of this signal over time, according to the same principles as those described above.

Note that, where appropriate, the above determination can be used by the processor 14 together with other parameters determined for the container 23, such as local parameters. For example, temperature sensors are also used.

Alternatively, the pressure sensor may be placed inside the container 23 rather than in the line 60, in which case the signal can be sent to the processor 14 through the port 31.

In the above examples, the envelope of the container 23 is substantially non-extensible.

In a second embodiment, more precise monitoring of the freezing state of the biopharmaceutical fluid can be obtained. As is apparent from the above description, the above method only allows qualifying the freezing state as one among three states (or four states, if also considering the initial state of the biopharmaceutical fluid at a temperature strictly above the temperature at which the transition to solid begins).

More precise monitoring can be obtained by quantifying the freezing state of the biopharmaceutical fluid. This variant requires the use of quantitative values. In particular, the quantitative parameter of interest is the amount of gas present in the container 23.

One particular example will be given in the context of an operation of freezing a biopharmaceutical fluid that is initially in the liquid state. The initial amount of gas in the container can be determined. This initial amount is determined by any suitable means. For example, it can be estimated from the inside volume of the container (this volume is generally known from manufacturing the container), the volume of biopharmaceutical fluid in the liquid state (this volume may be determined for example from the weight of container, the internal temperature of the container (which may be the ambient temperature or determined using a sensor), and a table giving the density of the biopharmaceutical fluid according to temperature)), the temperature (estimated as already mentioned), and the pressure measured by the pressure sensor 57.

If the density of the biopharmaceutical fluid is known in the liquid state and solid state at the transition temperature between these two phases, the proportion of biopharmaceutical fluid in the solid state can be determined from all these data.

Thus, by measuring the mass of outflowing gas (for example with a mass flowmeter), and knowing the initial mass of gas, the mass of gas remaining in the container 23 is known. As the pressure is also known from the pressure sensor 57, as well as the average temperature (known from a table), the volume of gas remaining in the container 23 is known. The macroscopic parameter can therefore be the amount of material (or mass) in its gas phase within the container.

One will note that there are many variants for determining the evolution of the freezing state of a biopharmaceutical fluid, based on a macroscopic parameter of the container 23. Other than the pressure in the headspace of the container 23, one could for example use the evolution in the total weight of the container 23, or the evolution in the total volume of the container 23, for example.

The various examples described above demonstrate in particular the detection of the end of the fluid transformation process between liquid phase and solid phase. Alternatively, one could be interested in more than that specific moment. For example, the same method could be used to determine when freezing begins. Indeed, the moment when freezing begins is clearly visible in FIG. 7 as being the moment before the outlet valve 80 starts to be controlled.

In one variant in which the container 23 is provided with a gas entry/exit port 30, progress in the freezing process is determined based on variations in the gas volume. At constant container volume, $dV_g/dt = -dV_h/dt$, where $d./dt$ indicates the derivative over time, $V_g$ the volume of ice, and $V_h$ the volume of gas.

Variations over time in the volume of gas $V_h$ can be determined from characterizing the flow of gas through the gas entry/exit port 30. This step is carried out during the freezing process.

The pressure regulation system is disabled. The gas entry/exit port 30 is open, and the pressure is allowed to decrease until it reaches a value OP2 (for example 5 millibar (mbar)) after transitioning through a value OP1 (for example 20 mbar) greater than OP2.

The duration $\Delta t$ of the gas release necessary between detection of the first level of positive pressure OP1 and detection of the second level of positive pressure OP2 by the pressure sensor 19 is determined by a timer. It is understood that the pressure sensor 19 can obtain several measurements close together of a gas parameter representative of the level of pressure in the internal filling volume, the output signals or one continuous output signal typically being delivered by the pressure sensor 19 to the monitoring device 4. For example, starting the operation of the timer is dependent on a signal indicating detection of the first level of positive pressure OP1, received by the monitoring device 4, while stopping the operation of the timer depends on a signal indicating detection of the second level of positive pressure OP2, received by the monitoring device 4.

In the present example, the duration $\Delta t$ of the gas release is 50 seconds. In one embodiment of the monitoring device 4, an algorithm is provided for calculating the internal gas filling volume, from the input parameters given above and from this duration $\Delta t$ of the gas release. A routine for implementing this algorithm is for example stored in memory and activated by the analysis system 62. The algorithm may carry out two successive calculation steps:

calculating a decay constant k, characteristic of the flow of released gas, according to the following equation:

$$k = -\ln(OP2/OP1)/\Delta t$$

where ln is the natural logarithm function;
calculating the internal gas filling volume by using the following correlation:

$$Vg = Q/k + Vc$$

where Q is a volumetric flow rate constant and Vc is a volume constant, these two constants Q and Vc being experimentally determined from experiments in which the internal volume Vg is already known for a similar container 23, during a prior calibration process. With the parameters Vg and the inverse 1/k being considered as inputs to the above linear regression, we experimentally obtain the constants Q and Vc as output values. The correlation corresponds to the physical gas flow model applicable to the release of gas through the gas entry/exit port 30 and via the associated gas release valve.

The two constants Q and Vc may specifically depend on the dimensions of the treatment station and/or on the biopharmaceutical fluid B filling parameters of the container 23 which can be considered as unchanging. For this correlation relating to the volume, obtained by simple linear regression, the constant Q is a slope or gradient (called the "volume estimator slope"), while the constant Vc is the intercept (called the "volume estimator intercept").

In experimental conditions where the constant Q was evaluated at 0.288 L/s (17.28 L/min) and the constant Vc was evaluated at 5.066 L, and for the above case where the duration $\Delta t$ of the gas release determined by the control unit 7 is 50 seconds to transition from 20 mbar to 5 mbar, calculation with the algorithm yields a value for k as follows:

$$k = -\ln(5/20)/50 = 0.00277 \text{ s}^{-1}$$

Next the internal filling volume Vg is estimated as 15.5 L using the following calculation, taking into account the values for constants Q and Vc as indicated above:

$$Vg = 0.288/0.0277 + 5.066$$

The pressure regulation system is restarted.

The above steps are reproduced over time to determine the volume of gas over time, and from this the volume of biopharmaceutical fluid over time. The volume of biopharmaceutical fluid is directly related to the progress of the freezing process. The time scale of the freezing process is large compared to the above process, which allows its repeated use without adversely affecting the freezing process itself.

The above methods have been described in the context of a freezing process. A similar method could be used as part of a thawing process. In particular, such a method may be useful in determining the start of the transformation from solid phase to liquid phase. This can be detected when the graph of the pressure over time transitions from a portion where gas is repeatedly released (due to expansion of the fluid in the solid state as the density decreases with temperature) to a portion where gas is allowed entry.

One can thus determine at any moment the freezing state of the biopharmaceutical fluid contained in the container 23. This information can be used to control the thermal treatment. For example, this information can be used to modify the thermal treatment (in particular to end the thermal treatment). For example, based on this information, the processor 14 can cause the thermal generator 9 to apply a different temperature profile to the applicator elements 8. For example, the processor 14 can compare the progress of the thermal treatment process to a predetermined profile stored in memory 13, and modify the thermal treatment according to the comparison. The stored predetermined profile corresponds, for example, to an average of the profiles obtained in previous thermal treatments, or to a desired target profile for the thermal treatment.

In another variant, based on this information the processor 14 can cause the thermal generator 9 to apply a particular locational distribution in the thermal treatment applied. For example, if the applicator elements 8 can be controlled independently, the processor 14 can cause the thermal generator 9 to apply a different thermal treatment to the various applicator elements. Thus, in the example in FIG. 4, it may be arranged that the two applicator elements 8 are controlled independently. The thermal treatment profile applied to each side face of the container 23 may therefore be different.

Referring again to FIG. 3, we have described a stand 44 accommodating a receptacle 5. As can be seen in FIG. 3, the stand 44 can accommodate several receptacles 5, placed for example adjacent to each other on the stand 44. In other words, the thermal treatment station can apply a thermal treatment to a plurality of containers 23 simultaneously.

A monitoring device may be provided for each container 23, to monitor the freezing state of the biopharmaceutical fluid contained in said container. Thus, each monitoring device is independently able to determine the freezing state of the biopharmaceutical fluid of its own container 23. Where appropriate, the same analysis system 62 is used for the different containers.

It may be arranged that the processor 14 applies a different thermal treatment to different containers 23, based on freezing state information sent from each container. When simultaneously processing a group of containers where some containers are more central and others are more peripheral, it is possible for the thermal profile within the different containers to differ, even if the applicators 8 associated with each container receive identical instructions. Also, the processor 14 may control the thermal generator 9 to generate different thermal treatments for the different containers 23.

The invention has been described above for a particular embodiment of the containing means 3 and thermal treatment station 2. However, the invention is not limited to these embodiments. Alternatively, other types of containing means and/or other types of thermal treatment station may be used.

For example, in one particular embodiment, the container 23 may be rigid or non-deformable. The pressure in the container 23 headspace can be used as the macroscopic parameter. In another particular embodiment, the envelope 25 of the container 23 can be extensible. A parameter combining the pressure in the headspace of the container 23 and the volume of the envelope can be used as the macroscopic parameter.

Figure 8:
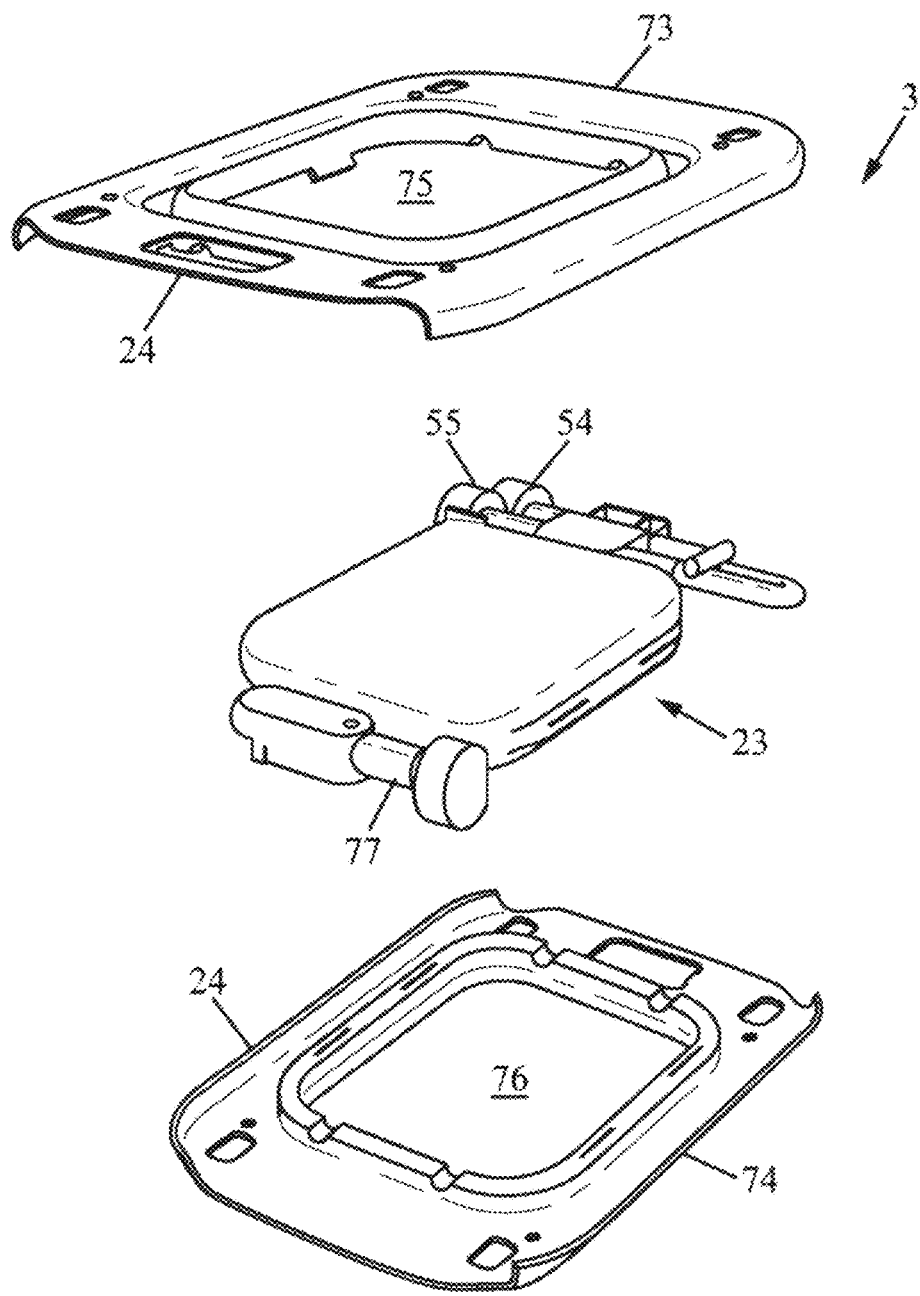
FIG. 8 is an exploded perspective view of a second embodiment of a biopharmaceutical fluid containing means.

FIG. 8 shows yet another exemplary embodiment of the containing means 3. As in the previous embodiments, the containing means comprises a container 23 and a structure 24. Here the structure 24 is made in two independent parts 73 and 74 that can be assembled together, the container 23 being arranged between the two parts 73 and 74. In this example, each part 73 is in the form of a shell forming a frame defining a central opening 75, 76 respectively, through which the container protrudes 23. The head portion of the container 23 is equipped with two lines for filling 54 and draining 55 which are arranged between the two parts 73 and 74 forming a shell and are protected by them. The carrier line 58 and the gas infeed line 60 are not represented in this example, but may be provided in parallel. The bottom part of the flexible container 23 may be equipped with a port 77 where a local temperature sensor or any other desired instrumentation may be mounted.

Figure 10:
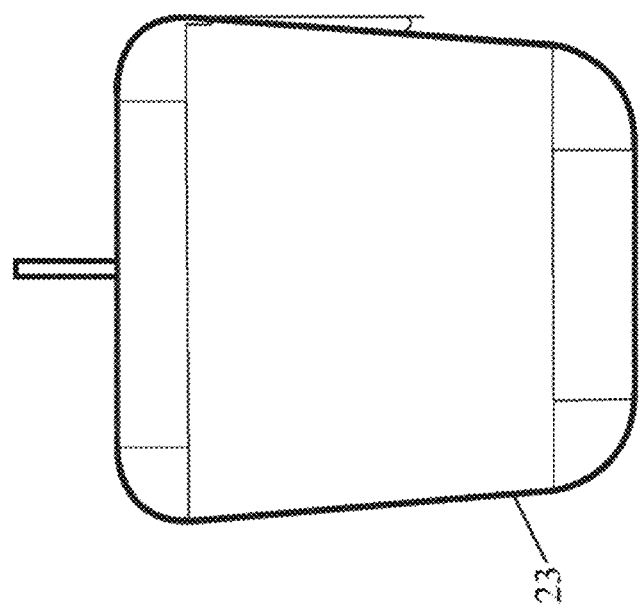
FIG. 10 is a front view of FIG. 9.
Figure 9:
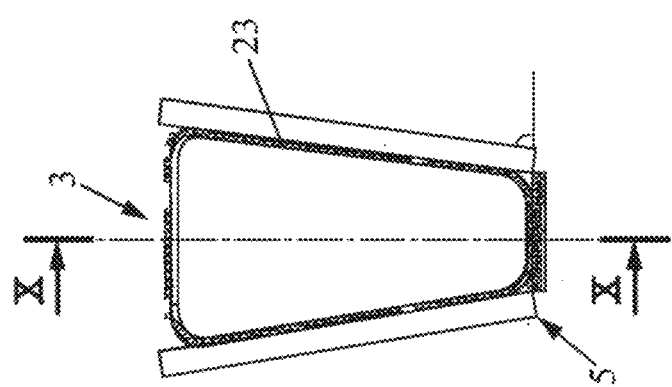
FIG. 9 is a schematic side view of a portion of yet another example of a thermal treatment system.

FIGS. 9 and 10 show yet another alternative embodiment, respectively in a side view and front view. In this embodiment, one difference from the preceding examples is that the receptacle 5 of the thermal treatment station has, in a cross-sectional view, a shape that flares slightly outward in the upward direction along the vertical axis. The containing means 3 may have a shape appropriate for this form of receptacle. In particular, the container 23 may have a greater width in its upper portion than in its lower portion. In addition, as can be seen in FIG. 10, the receptacle 5 of the thermal treatment station may also have, in an orthogonal cross-sectional view, a shape flaring slightly outward in the upward direction along the vertical axis. The containing means 3 may have a shape appropriate for this form of receptacle. In particular, the container 23 may also have a greater width in its upper portion than in its lower portion in this view. The structure 24 of the containing means 3 is appropriate for the shape of the container 23. The advantage of this flared shape is that it provides better control of how the freezing front spreads during the fluid's transition from the liquid state to the solid state during cold treatment.

The invention claimed is:

1. Monitoring device for monitoring the freezing state of a biopharmaceutical fluid in a container intended to receive a biopharmaceutical fluid that is to transition between the liquid state and the frozen state, wherein the device comprises a peripheral envelope made of plastic, intended and suitable for association with a thermal treatment receptacle,
wherein the device further comprises a sensor suitable for non-intrusively detecting a control parameter which is a macroscopic parameter of the container, and an analysis system suitable for determining a freezing state of the biopharmaceutical fluid on the basis of the macroscopic parameter of the container, the macroscopic parameter being derived directly or indirectly from an average density of a non-gaseous portion of contents of the container.

2. Monitoring device according to claim 1, wherein the sensor is adapted to detect a value of the control parameter repeatedly over time during the thermal treatment process.

3. Monitoring device according to claim 2, wherein the parameter values over time show an abrupt change when there is a change in the freezing state of the biopharmaceutical fluid, and wherein the analysis system is adapted to detect this abrupt change.

4. Monitoring device according to claim 3, wherein the parameter values over time show an abrupt change when transitioning between a state where a portion of the biopharmaceutical fluid is not frozen and a state where the entire biopharmaceutical fluid is frozen.

5. Monitoring device according to claim 3, wherein the parameter values over time show an abrupt change when transitioning between a state where the entire biopharmaceutical fluid is not frozen and a state where a portion of the biopharmaceutical fluid is frozen.

6. Monitoring device according to claim 1, wherein the analysis system is adapted to determine a frozen state of the biopharmaceutical fluid on the basis of an absolute value of the control parameter.

7. Monitoring device according to claim 6, wherein the analysis system is adapted to determine the frozen state of the biopharmaceutical fluid on the basis of an initial value of the control parameter, and of a change over time in the absolute value of the control parameter determined from the sensor.

8. Monitoring device according to claim 1, wherein the non-gaseous portion comprise one and/or the other among a liquid phase and a solid phase, the container possibly further containing a gaseous phase.

9. Monitoring device according to claim 1, wherein the control parameter is the gas pressure in an upper portion of the container arranged above the biopharmaceutical fluid in an end head portion of the container, said portion being filled with a gas.

10. Monitoring device according to claim 1, comprising a gas entry/exit line adapted to be associated in a fluidtight communication with a gas entry/exit port of the container, said port being located in an upper portion of the container arranged above the biopharmaceutical fluid in an end head portion of the container, said portion being filled with a gas, the sensor being suitable for determining a parameter of the headspace.

11. Monitoring device according to claim 10, the control parameter being the amount of gas in the headspace, the volume of gas in the head space, or the volume of biopharmaceutical fluid in the container.

12. Monitoring device according to claim 10, further comprising an opening/closing valve associated with the gas entry/exit port.

13. Monitoring device according to claim 10, wherein the sensor comprises a pressure sensor intended and suitable for measuring or monitoring the gas pressure in the upper portion or in the gas entry/exit line, and a regulation system intended and suitable for controlling the entry/release of gas into/from the upper portion via the gas entry/exit port and the gas entry/exit line, according to a desired pressure profile in the headspace.

14. Monitoring device according to claim 13, further comprising a means intended and suitable for allowing the entry/release of gas into/from the headspace, via the gas entry/exit port and the gas entry/exit line.

15. Monitoring device according to claim 14, wherein the regulation system intended and suitable for controlling the entry/release of gas into/from the upper portion, via the gas entry/exit port and the gas entry/exit line, operates so as to allow the entry of gas when the gas pressure in the upper portion decreases and to release gas when the gas pressure in the upper portion increases.

16. Monitoring device according to claim 1, further comprising a control system suitable for thermally controlling the freezing receptacle according to the freezing state determined by the analysis system.

17. Thermal treatment system for a biopharmaceutical fluid, comprising a thermal treatment receptacle intended and suitable for receiving a container of biopharmaceutical fluid, and a monitoring device according to claim 1.

18. Thermal treatment system according to claim 17, comprising a plurality of thermal applicators in the receptacle, independently controllable, and wherein the control system independently controls said thermal applicators.

19. System according to claim 17, comprising a plurality of thermal treatment receptacles each intended and suitable for receiving a respective container of biopharmaceutical fluid, each receptacle being independently controllable by the control system, wherein the control system is adapted to control each thermal treatment receptacle independently according to the freezing state determined for each container.

20. Method for monitoring the freezing state of a biopharmaceutical fluid in a container intended to receive a biopharmaceutical fluid that is to transition between the liquid state and the frozen state, comprising a peripheral envelope of plastic, intended and suitable for association with a thermal treatment receptacle, wherein a sensor non-intrusively detects a control parameter which is a macroscopic parameter of the container, and an analysis system determines a freezing state of the biopharmaceutical fluid on the basis of the macroscopic parameter of the container, the macroscopic parameter being derived directly or indirectly from an average density of a non-gaseous portion of contents of the container.

* * * * *